(12) United States Patent
Ellsworth et al.

(10) Patent No.: US 6,515,117 B2
(45) Date of Patent: Feb. 4, 2003

(54) C-ARYL GLUCOSIDE SGLT2 INHIBITORS AND METHOD

(75) Inventors: Bruce Ellsworth, Princeton, NJ (US); William N. Washburn, Titusville, NJ (US); Philip M. Sher, Plainsboro, NJ (US); Gang Wu, Princeton, NJ (US); Wei Meng, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/151,436

(22) Filed: May 20, 2002

(65) Prior Publication Data

US 2002/0137903 A1 Sep. 26, 2002

Related U.S. Application Data

(63) Continuation-in-part of application No. 09/679,027, filed on Oct. 4, 2000, now Pat. No. 6,414,126.
(60) Provisional application No. 60/194,615, filed on Apr. 5, 2000, and provisional application No. 60/158,773, filed on Oct. 12, 1999.

(51) Int. Cl.[7] .................. C07H 15/20; A61K 31/70
(52) U.S. Cl. .................. 536/17.2; 536/1.11; 536/17.3; 536/17.4; 536/17.5; 536/18.4; 514/866; 514/25
(58) Field of Search .................. 536/1.11, 17.2, 536/17.3, 17.4, 17.5, 18.4; 514/866, 25

(56) References Cited

U.S. PATENT DOCUMENTS 6,414,126 B1 * 7/2002 Ellsworth et al. .......... 536/17.2

FOREIGN PATENT DOCUMENTS

| EP | 0 598359 A | 5/1994 |
|----|-----------|--------|
| EP | 0 684 254 B1 | 11/1995 |
| EP | 0 773 226 B1 | 5/1997 |
| EP | 0 850 948 A1 | 1/1998 |
| JP | 8-27006 | 1/1996 |
| JP | 9124685 | 7/1997 |
| JP | 9188625 | 7/1997 |
| JP | 10245391 | 9/1998 |
| JP | 9124684 | 5/1999 |
| WO | WO 9831697 A | 7/1998 |
| WO | WO 98/31697 * | 7/1998 |
| WO | WO 0 018918 | 4/2000 |

OTHER PUBLICATIONS

T. Kuribayashi et al., Journal of Carbohydrate Chemistry, (1999) vol. 18, No. 4, pp. 371–382.
W. Gaffield et al., Tetrahedron, (1978) vol. 34, No. 20, pp. 3089–3096.
Benhaddou et al. Carbohydrate Research 260 (1994) pp. 243–250.
Hongu et al. Chemical Phar. Bull. (1998) vol. 46, No. 10, pp. 1545–1565.
Tsujihara et al. Chemical Pharm. Bull. (1996) vol. 44. No. 6. pp. 1174–1180.
Hongu et al. Chem. Pharm. Bull. (1998) vol. 46. No. 1, pp. 22–23.
Oku et al. Diabetes. vol. 48 (1999) pp. 1794–1800.

* cited by examiner

*Primary Examiner*—Samuel Barts
*Assistant Examiner*—Devesh Khare
(74) *Attorney, Agent, or Firm*—Jonathan Provoost; Burton Rodney

(57) ABSTRACT

An SGLT2 inhibiting compound is provided having the formula

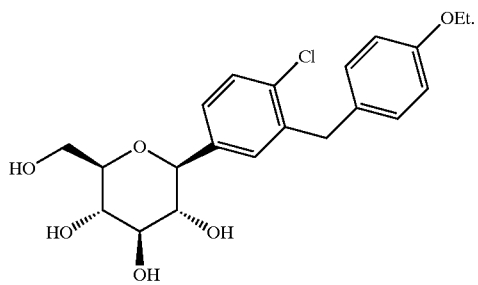

A method is also provided for treating diabetes and related diseases employing an SGLT2 inhibiting amount of the above compound alone or in combination with another antidiabetic agent or other therapeutic agent.

17 Claims, No Drawings

C-ARYL GLUCOSIDE SGLT2 INHIBITORS AND METHOD

This application is a continuation-in-part under 37 C.F.R. §1.53(b)(2) of U.S. Ser. No. 09/679,027, filed Oct. 4, 2000, which claims the benefit of provisional application 60/194,615, filed Apr. 5, 2000 and provisional application 60/158,773, filed Oct. 12, 1999.

FIELD OF THE INVENTION

The present invention relates to C-aryl glucosides which are inhibitors of sodium dependent glucose transporters found in the intestine and kidney (SGLT2) and to a method for treating diabetes, especially type II diabetes, as well as hyperglycemia, hyperinsulinemia, obesity, hypertriglyceridemia, Syndrome X, diabetic complications, atherosclerosis and related diseases, employing such C-aryl glucosides alone or in combination with one, two or more other type antidiabetic agent and/or one, two or more other type therapeutic agents such as hypolipidemic agents.

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney would be expected to aid in the normalization of plasma glucose levels, and perhaps body weight, by enhancing glucose excretion.

The development of novel, safe, and orally active antidiabetic agents is also desired in order to complement existing therapies, including the sulfonylureas, thiazolidinediones, metformin, and insulin, and to avoid the potential side effects associated with the use of these other agents.

Hyperglycemia is a hallmark of type II diabetes (NIDDM); consistent control of plasma glucose levels in diabetes can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. The SGLT specific inhibitor phlorizin or closely related analogs inhibit this reuptake process in diabetic rodents and dogs resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity, and delaying the development of diabetic complications.

Ninety percent of glucose reuptake in the kidney occurs in the epithelial cells of the early S1 segment of the renal cortical proximal tubule, and SGLT2 is likely to be the major transporter responsible for this reuptake. SGLT2 is a 672 amino acid protein containing 14 membrane-spanning segments that is predominantly expressed in the early S1 segment of the renal proximal tubules. The substrate specificity, sodium dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2. SGLT2 is a candidate gene for some forms of familial glucosuria, a genetic abnormality in which renal glucose reabsorption is impaired to varying degrees. None of these syndromes investigated to date map to the SGLT2 locus on chromosome 16. However, the studies of highly homologous rodent SGLTs strongly implicate SGLT2 as the major renal sodium-dependent transporter of glucose and suggest that the glucosuria locus that has been mapped encodes an SGLT2 regulator. Inhibition of SGLT2 would be predicted to reduce plasma glucose levels via enhanced glucose excretion in diabetic patients.

SGLT1, another Na-dependent glucose cotransporter that is 60% identical to SGLT2 at the amino acid level, is expressed in the small intestine and in the more distal S3 segment of the renal proximal tubule. Despite their sequence similarities, human SGLT1 and SGLT2 are biochemically distinguishable. For SGLT1, the molar ratio of $Na^+$ to glucose transported is 2:1, whereas for SGLT2, the ratio is 1:1. The $K_m$ for $Na^+$ is 32 and 250–300 mM for SGLT1 and SGLT2, respectively. $K_m$ values for uptake of glucose and the nonmetabolizable glucose analog α-methyl-D-glucopyranoside (AMG) are similar for SGLT1 and SGLT2, i.e. 0.8 and 1.6 mM (glucose) and 0.4 and 1.6 mM (AMG) for SGLT1 and SGLT2 transporters, respectively. However, the two transporters do vary in their substrate specificities for sugars such as galactose, which is a substrate for SGLT1 only.

Administration of phlorizin, a specific inhibitor of SGLT activity, provided proof of concept in vivo by promoting glucose excretion, lowering fasting and fed plasma glucose, and promoting glucose utilization without hypoglycemic side effects in several diabetic rodent models and in one canine diabetes model. No adverse effects on plasma ion balance, renal function or renal morphology have been observed as a consequence of phlorizin treatment for as long as two weeks. In addition, no hypoglycemic or other adverse effects have been observed when phlorizin is administered to normal animals, despite the presence of glycosuria. Administration of an inhibitor of renal SGLTs for a 6-month period (Tanabe Seiyaku) was reported to improve fasting and fed plasma glucose, improve insulin secretion and utilization in obese NIDDM rat models, and offset the development of nephropathy and neuropathy in the absence of hypoglycemic or renal side effects.

Phlorizin itself is unattractive as an oral drug since it is a nonspecific SGLT1/SGLT2 inhibitor that is hydrolyzed in the gut to its aglycone phloretin, which is a potent inhibitor of facilitated glucose transport. Concurrent inhibition of facilitative glucose transporters (GLUTs) is undesirable since such inhibitors would be predicted to exacerbate peripheral insulin resistance as well as promote hypoglycemia in the CNS. Inhibition of SGLT1 could also have serious adverse consequences as is illustrated by the hereditary syndrome glucose/galactose malabsorption (GGM), in which mutations in the SGLT1 cotransporter result in impaired glucose uptake in the intestine, and life-threatening diarrhea and dehydration. The biochemical differences between SGLT2 and SGLT1, as well as the degree of sequence divergence between them, allow for identification of selective SGLT2 inhibitors.

The familial glycosuria syndromes are conditions in which intestinal glucose transport, and renal transport of other ions and amino acids, are normal. Familial glycosuria patients appear to develop normally, have normal plasma glucose levels, and appear to suffer no major health deficits as a consequence of their disorder, despite sometimes quite high (110–114 g/daily) levels of glucose excreted. The major symptoms evident in these patients include polyphagia, polyuria and polydipsia, and the kidneys appear to be normal in structure and function. Thus, from the evidence available thus far, defects in renal reuptake of glucose appear to have minimal long term negative consequences in otherwise normal individuals.

The following references disclose C-aryl glucosides SGLT2 inhibitors for treating diabetes.

WO 01/27128 discloses compounds of the structure

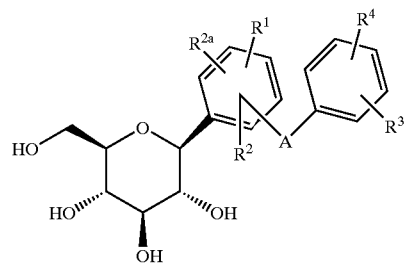

where

A is O, S, NH, or $(CH_2)_n$ where n is 0–3;

$R^1$, $R^2$ and $R^{2a}$ are independently hydrogen, OH, $OR^5$, alkyl, $CF_3$, $OCHF_2$, $OCF_3$, $SR^{5i}$ or halogen, etc;

$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, etc. These compounds are reported to be inhibitors of the SGLT2 transporter and consequently represent a mode for treatment of diabetes and complications thereof.

WO 98/31697 discloses compounds of the structure

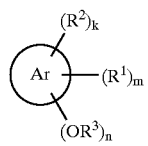

Where Ar includes, among others, phenyl, biphenyl, diphenylmethane, diphenylethane, and diphenylether, and $R^1$ is a glycoside, $R^2$ is H, OH, amino, halogen, carboxy, alkyl, cycloalkyl, or carboxamido, and $R^3$ is hydrogen, alkyl, or acyl, and k, m, and n are independently 1–4. A subset of compounds disclosed in WO 98/31697 contains compounds of the following structures

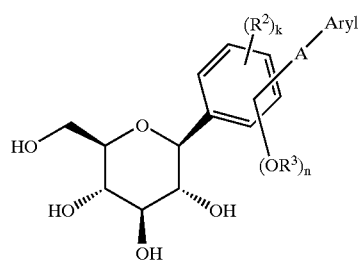

A or O or $(CH_3)_x$ where x = 0–3
$R^3$ is hydrogen, alkyl or acyl group where n is 1–4
$R^2$ is hydrogen, alkyl, OH, $NH_2$, halogen, $CO_2H$ or carboximide where k is 1–4 which are disclosed for use in the treatment or prevention of inflammatory diseases, autoimmune diseases, infections, cancer, and cancer metastasis, reperfusion disorders, thrombosis, ulcer, wounds, osteoporosis, diabetes mellitus and atherosclerosis, among others.

DESCRIPTION OF THE INVENTION

In accordance with the present invention, a C-aryl glucoside compound is provided which has the structure

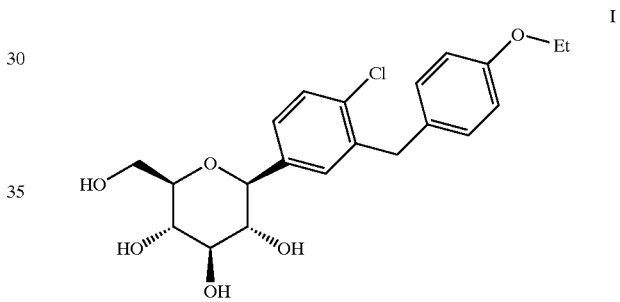

including pharmaceutically acceptable salts thereof, all stereoisomers thereof, and all prodrug esters thereof.

The compound of formula I possesses activity as inhibitors of the sodium dependent glucose transporters found in the intestine and kidney of mammals and is useful in the treatment of diabetes and the micro- and macrovascular complications of diabetes such as retinopathy, neuropathy, nephropathy, and wound healing.

The present invention provides for compound of formula I, pharmaceutical compositions employing such a compound and for methods of using such a compound.

In addition, in accordance with the present invention, a method is provided for treating or delaying the progression or onset of diabetes, especially type I and type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type of antidiabetic agent and/or another type of therapeutic agent such as a hypolipidemic agent is administered to a human patient in need of treatment.

The conditions, diseases, and maladies collectively referred to as "Syndrome X" (also known as Metabolic Syndrome) are detailed in Johannsson *J. Clin. Endocrinol. Metab.*, 82, 727–34 (1997).

The term "other type of therapeutic agents" as employed herein refers to one or more antidiabetic agents (other than SGLT2 inhibitors of formula I), one or more anti-obesity agents, anti-hypertensive agents, anti-platelet agents, anti-atherosclerotic agents and/or one or more lipid-lowering agents (including anti-atherosclerosis agents).

In the above method of the invention, the compound of structure I of the invention will be employed in a weight ratio to the one, two or more antidiabetic agent and/or one, two or more other type therapeutic agent (depending upon its mode of operation) within the range from about 0.01:1 to about 300:1, preferably from about 0.1:1 to about 10:1.

DETAILED DESCRIPTION OF THE INVENTION

The compound of formula I of the invention can be prepared as shown in the following reaction scheme and description thereof wherein temperatures are expressed in degrees Centigrade.

Compound of formula I can be prepared as shown in Scheme 1 by treatment of compound of formula II

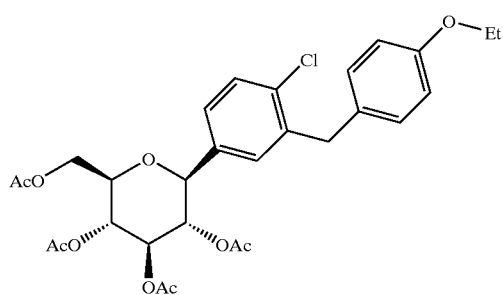

II with a base such as LiOH or NaOH in a solvent such as a 1:2:3 mixture of H₂O/THF/MeOH or aq. MeOH or aq. EtOH.

The compound of formula II (which is a novel intermediate that readily crystallizes) provides a convenient means to purify crude compound of formula Ia which was obtained as a mixture of α and β anomers.

The compound of formula II can be prepared by treatment of compound of formula Ia with Ac₂O in a solvent such as CH₂Cl₂ containing pyridine and a catalyst such as dimethylaminopyridine (DMAP).

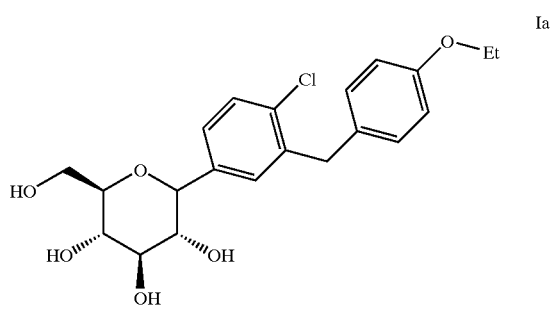

Ia

Compounds of formula Ia can be prepared by reduction of a compound of formula III with a reducing agent such as Et₃SiH in a solvent such as 1:1 CH₂Cl₂/MeCN at –10° in the presence of a Lewis acid catalyst such as BF₃.Et₂O.

III

The compound of formula II can alternatively be prepared from compound of formula III by first acetylating compound of formula III with Ac₂O in a solvent such toluene or CH₂Cl₂ containing a base such as Hunig's base or Et₃N and a catalyst such as DMAP to generate compound of formula IV.

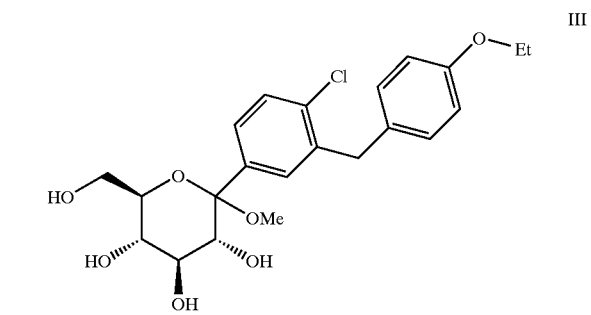

IV

Subsequent conversion of compound of formula IV to compound of formula II can be achieved by treatment at 20° treatmentwith a reducing agent such as Et₃SiH in a solvent such as MeCN containing 1 equiv of H₂O and a Lewis acid catalyst such as BF₃.Et₂O.

Scheme 1

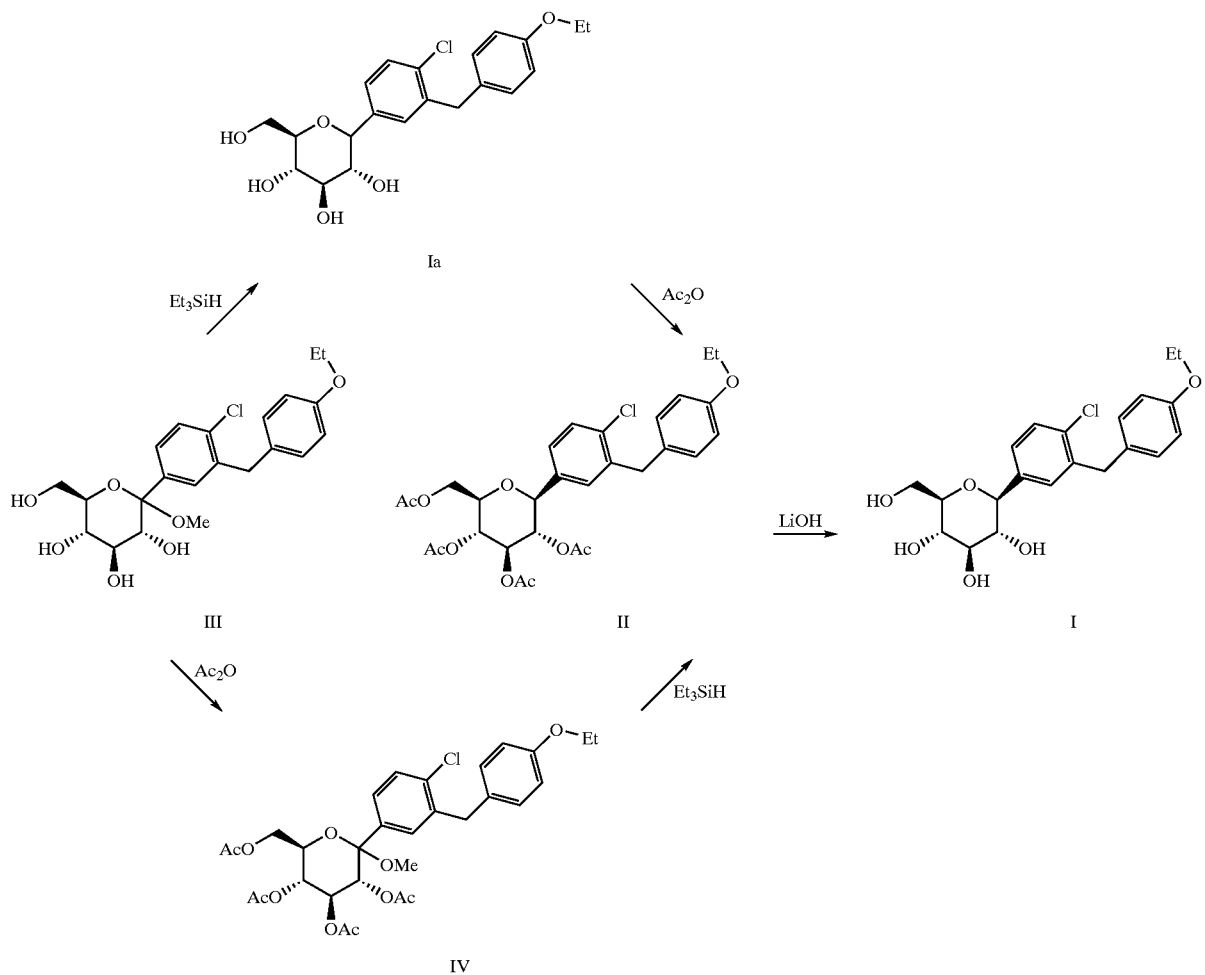

The compound of formula III can be prepared, as outlined in Scheme 2, by 1) addition of a cold THF solution of an aryl lithium of formula V to a persilylated gluconolactone of formula VI in a solvent such as toluene at −75°. Subsequently, a methanol solution of a protic acid such methanesulfonic acid (MSA) is added after 30 min and the solution stirred at 20° until transformation of the intermediary lactol to III is complete.

The compound of formula VI can be prepared by treatment of commercially available D-gluconolactone with a silylating agent such as trimethylsilyl chloride in a solvent such as THF containing a base such as N-methylmorpholine.

The compound of formula V can be prepared by treatment of compound of formula VII with an alkyl lithium such as n-BuLi or t-BuLi in a solvent such as THF at −75°.

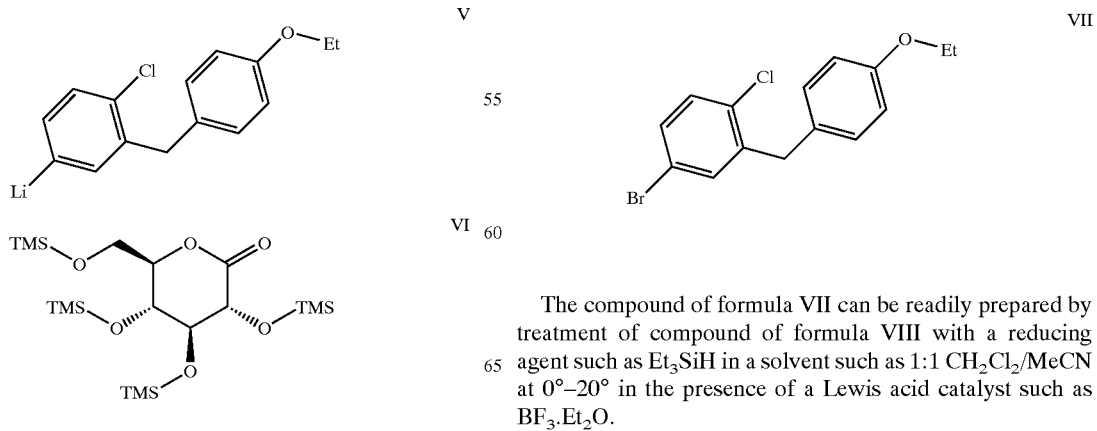

The compound of formula VII can be readily prepared by treatment of compound of formula VIII with a reducing agent such as $Et_3SiH$ in a solvent such as 1:1 $CH_2Cl_2$/MeCN at 0°–20° in the presence of a Lewis acid catalyst such as $BF_3 \cdot Et_2O$.

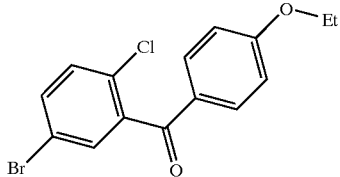

VIII

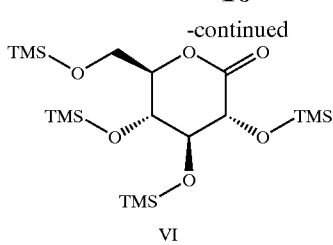

VI

The compound of formula VIII can be prepared by Friedel-Craft acylation of commercially available ethoxybenzene (phenetole) with 2-chloro-5-bromobenzoyl chloride in a solvent such as $CH_2Cl_2$ containing an equivalent of a Lewis Acid such as $AlCl_3$ or $AlBr_3$.

2-Chloro-5-bromobenzoyl chloride is readily prepared from commercially available 2-chloro-5-bromobenzoic acid by treatment with oxalyl chloride in a solvent such as $CH_2Cl_2$ containing a catalytic amount of DMF.

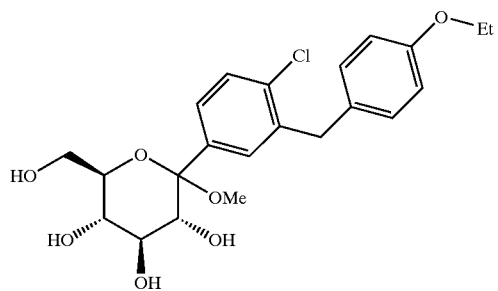

III

Listed below are definitions of various terms used in the description of the instant invention. These definitions apply to the terms as they are used throughout the specification (unless they are otherwise limited in specific instances) either individually or as part of a larger group.

The following abbreviations are employed herein:

Ph=phenyl
Bn=benzyl
t-Bu=tertiary butyl
Me=methyl
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent

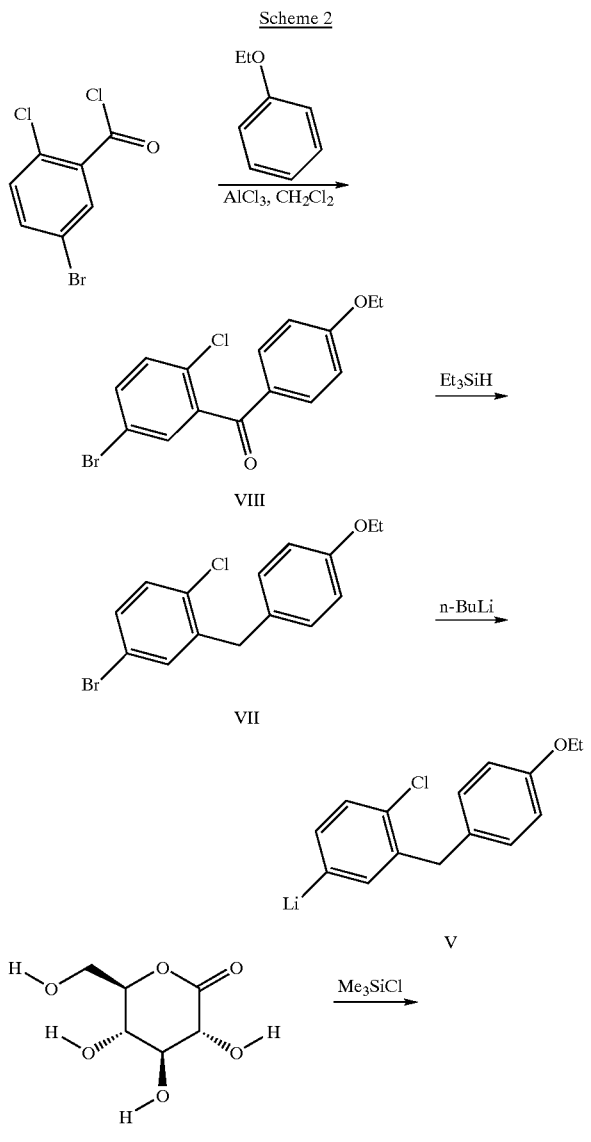

RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

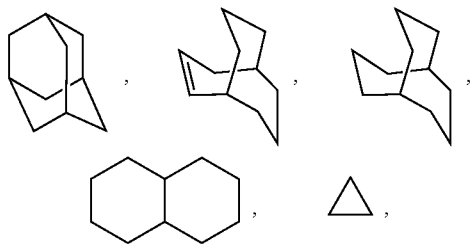

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the alkyl substituents.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

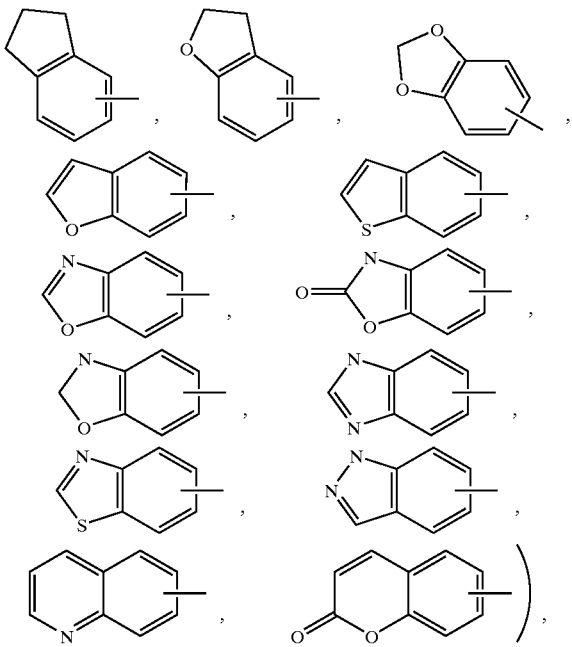

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include

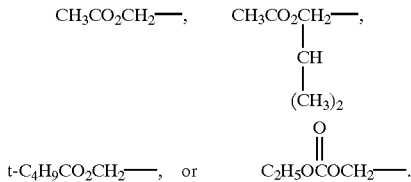

Where the compound of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compound of the instant invention are contemplated, either in admixture or in pure or substantially pure form. The compound of the present invention can have asymmetric centers at any of the carbon atoms including any one of the R substituents. Consequently, compound of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compound of structure I may be used in combination with one or more other types of antidiabetic agents and/or one or more other types of therapeutic agents which may be administered orally in the same dosage form, in a separate oral dosage form or by injection.

The other type of antidiabetic agent which may be optionally employed in combination with the SGLT2 inhibitor of formula I may be 1,2,3 or more antidiabetic agents or antihyperglycemic agents including insulin secretagogues or insulin sensitizers, or other antidiabetic agents preferably having a mechanism of action different from SGLT2 inhibition and may include biguanides, sulfonyl ureas, glucosidase inhibitors, PPAR γ agonists such as thiazolidinediones, aP2 inhibitors, PPAR α/γ dual agonists, dipeptidyl peptidase IV (DP4) inhibitors, and/or meglitinides, as well as insulin, glucagon-like peptide-1 (GLP-1), PTP1B inhibitors, glycogen phosphorylase inhibitors and/or glucos-6-phosphatase inhibitors.

The other types of therapeutic agents which may be optionally employed in combination with the SGLT2 inhibitor of formula I include anti-obesity agents, antihypertensive agents, antiplatelet agents, antiatherosclerotic agents and/or lipid lowering agents.

The SGLT2 inhibitor of formula I may also be optionally employed in combination with agents for treating complications of diabetes. These agents include PKC inhibitors and/or AGE inhibitors.

It is believed that the use of the compound of structure I in combination with 1, 2, 3 or more other antidiabetic agents produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compound of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compound of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compound of structure I will be employed in a weight ratio to the glucosidase inhibitor within the range from about 0.01:1 to about 100:1, preferably from about 0.5:1 to about 50:1.

The compound of structure I may be employed in ombination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compound of structure I will be employed in a weight ratio to the thiazolidinedione in an amount within the range from about 0.01:1 to about 100:1, preferably from about 0.2:1 to about 10:1.

The sulfonyl urea and thiazolidinedione in amounts of less than about 150 mg oral antidiabetic agent may be incorporated in a single tablet with the compound of structure I.

The compound of structure I may also be employed in combination with an antihyperglycemic agent such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, (attorney file LA29) the disclosure of which is incorporated herein by reference, employing dosages as set out therein, which compounds designated as preferred are preferred for use herein.

The other antidiabetic agent may be an aP2 inhibitor such as disclosed in U.S. application Ser. No. 09/391,053, filed Sep. 7, 1999, and in U.S. provisional application No. 60/127, 745, filed Apr. 5, 1999 (attorney file LA27*), employing dosages as set out herein. Preferred are the compounds designated as preferred in the above application.

The other antidiabetic agent may be a DP4 inhibitor such as disclosed in WO99/38501, WO99/46272, WO99/67279 PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The SGLT2 inhibitor of formula I will be employed in a weight ratio to the meglitinide, PPAR γ agonist, PPAR α/γ dual agonist, aP2 inhibitor or DP4 inhibitor within the range from about 0.01:1 to about 100:1, preferably from about 0.2:1 to about 10:1.

The hypolipidemic agent or lipid-lowering agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications. All of the above U.S. Patents and applications are incorporated herein by reference.

The hypolipidemic agent may be an HMG CoA reductase inhibitor which includes, but is not limited to, mevastatin and related compounds as disclosed in U.S. Pat. No. 3,983, 140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. The hypolipidemic agent may also be the compounds disclosed in U.S. provisional application Nos. 60/211,594 and 60/211,595. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647, 576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and rosuvastatin.

The above-mentioned U.S. patents are incorporated herein by reference. The amounts and dosages employed will be as indicated in the Physician's Desk Reference and/or in the patents set out above.

The compound of formula I of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agents are pravastatin, simvastatin, lovastatin, atorvastatin, fluvastatin, cerivastatin, atavastatin and rosuvastatin.

When the other type of therapeutic agent which may be optionally employed with the SGLT2 inhibitor of formula I is 1, 2, 3 or more of an anti-obesity agent, it may include a beta 3 adrenergic agonist, a lipase inhibitor, a serotonin (and dopamine) reuptake inhibitor, a thyroid receptor beta drug, an anorectic agent, an NPY antagonist, a Leptin analog and/or an MC4 agonist.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

Examples of the anti-platelet agent(s) which may be optionally employed in combinations of this invention include abciximab, ticlopidine, eptifibatide, dipyridamole, aspirin, anagrelide, tirofiban and/or clopidogrel.

Examples of the anti-hypertensive agent(s) which may be optionally employed in combinations of this invention include ACE inhibitors, calcium antagonists, alpha-blockers, diuretics, centrally acting agents, angiotensin-II antagonists, beta-blockers and vasopeptidase inhibitors.

Examples of ACE inhibitors include lisinopril, enalapril, quinapril, benazepril, fosinopril, ramipril, captopril, enalaprilat, moexipril, trandolapril and perindopril; examples of calcium antagonists include amlodipine, diltiazem, nifedipine, verapamil, felodipine, nisoldipine, isradipine and nicardipine; examples of alpha-blockers include terazosin, doxazosin and prazosin; examples of diuretics include hydrochlorothiazide, torasemide, furosemide, spironolactone and indapamide; examples of centrally acting agents include clonidine and guanfacine; examples of angiotensin-II antagonists include losartan, valsartan, irbesartan, candesartan and telmisartan; examples of beta-blockers include metoprolol, propranolol, atenolol, carvedilol and sotalol; and examples of vasopeptidase inhibitors include omapatrilat and gemopatrilat.

In carrying out the method of the invention, a pharmaceutical composition will be employed containing the compound of structure I, with or without another antidiabetic agent and/or antihyperlipidemic agent, or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations, or they can be administered intranasally or in transdermal patches. The dose for adults is preferably between 10 and 2,000 mg per day, which can be administered in a single dose or in the form of individual doses from 1–4 times per day.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

SGLT2 inhibitor activity of the compounds of the invention may be determined by use of an assay system as set out below.

Assay for SGLT2 Activity

The mRNA sequence for human SGLT2 (GenBank #M95549) was cloned by reverse-transcription and amplification from human kidney mRNA, using standard molecular biology techniques. The cDNA sequence was stably transfected into CHO cells, and clones were assayed for SGLT2 activity essentially as described in Ryan et al. (1994). Evaluation of inhibition of SGLT2 activity in a clonally selected cell line was performed essentially as described in Ryan et al., with the following modifications. Cells were grown in 96-well plates for 2–4 days to 75,000 or 30,000 cells per well in F-12 nutrient mixture (Ham's F-12), 10% fetal bovine serum, 300 ug/ml Geneticin and penicillin-streptomycin. At confluence, cells were washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells then were incubated with 10 $\mu$M [$^{14}$C]AMG, and 10 $\mu$M inhibitor (final DMSO=0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hr. Uptake assays were quenched with ice cold 1×PBS containing 0.5 mM phlorizin, and cells were then lysed with 0.1% NaOH. After addition of MicroScint scintillation fluid, the cells were allowed to shake for 1 hour, and then [$^{14}$C]AMG was quantitated on a TopCount scintillation counter. Controls were performed with and without NaCl. For determination of $EC_{50}$ values, 10 inhibitor concentrations were used over 2 log intervals in the appropriate response range, and triplicate plates were averaged across plates.

Ryan M J, Johnson G, Kirk J, Fuerstenberg S M, Zager R A and Torok-Storb B. 1994. HK-2: an immortalized proximal tubule epithelial cell line from normal adult human kidney. Kidney International 45: 48–57.

The following Working Examples represent preferred embodiments of the present invention. All temperatures are expressed in degrees Centigrade unless otherwise indicated.

EXAMPLE

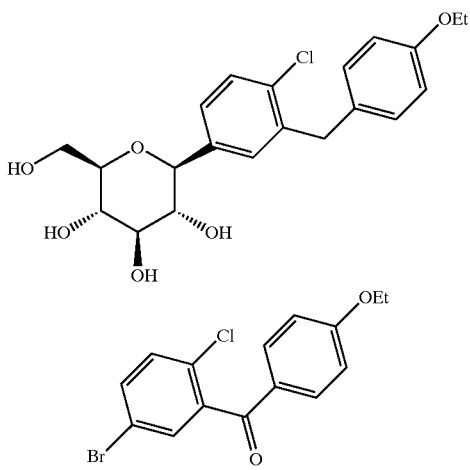

A. 5-Bromo-2-chloro-4'-ethoxybenzophenone

To a stirred suspension of commercial 5-bromo-2-chlorobenzoic acid (250 g, 1.06 mol) in 450 mL of $CH_2Cl_2$ containing oxalyl chloride (1.1 mol) was added 1.5 mL of DMF. Once the vigorous evolution of gas ceased, the reaction was stirred overnight prior to removal of the volatiles under vacuum using a rotary evaporator. After dissolving the crude 5-bromo-2-chlorobenzoyl chloride in 200 ml of $CH_2Cl_2$, the yellow solution was transferred to a 2 L 3-neck flask equipped with an overhead stirrer and an internal thermometer. The stirred mixture was cooled to $-3°$ prior to adding phenetole (130 g, 1.08 mol). $AlCl_3$ (140 g, 1.07 mol) was added via a solid addition funnel over 30 min to insure that the temperature did not exceed 4°. The copious amounts of HCl gas which began to evolve after 60% of the $AlCl_3$ had been added were trapped by passing the gas over a stirred conc. NaOH solution. HPLC revealed the reaction to be 95% complete 10 minutes after the addition was finished. After the mixture was stirred at 4° for 1 hr, the reaction was quenched by pouring over ice. Subsequently, the suspension was diluted with $H_2O$ (1 L) and extracted 3× with $CH_2Cl_2$. The combined organic extracts were washed 2× with 1N HCl, 1× with $H_2O$, 2× with 1M NaOH, and 2× with brine prior to drying over $Na_2SO_4$. After removal of the volatiles, HPLC revealed the residue to be a 1:7 mixture of ortho/para isomers. Recrystallization 2× from 400 mL of absolute EtOH yielded 230 g (64%) of 5-bromo-2-chloro-4'-ethoxybenzophenone.

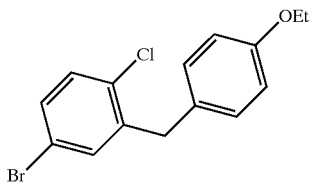

B. 5-Bromo-2-chloro-4'-ethoxydiphenylmethane

To a stirred solution of $Et_3SiH$ (400 mL, 2.51 mol and 5-bromo-2-chloro-4'-ethoxybenzophenone (390 g, 1.15 mol) in 900 mL of a 1:2 mixture 1,2-dichloroethane/MeCN at 10° C. was added $BF_3.Et_2O$ (150 mL, 1.58 mol) at such a rate that the temperature did not exceed 20°. Caution a moderate exotherm insues during the addition. After stirring overnight at 20° C., HPLC revealed the reaction to be 90% complete. After adding an additional 40 mL $Et_3SiH$ and 15 mL of $BF_3.Et_2O$, the reaction was heated to 50° for 3 hr. (Note elevated temperatures increase formation of the Ritter reaction product N-acetyl 5-bromo-2-chloro-4'-ethoxydiphenylmethylamine). Upon cooling, the reaction was quenched with 120 g of KOH in 300 mL of $H_2O$. After stirring 2 hr, the layers were separated. The aqueous layer was extracted 2× with $CH_2Cl_2$; the combined organic layers were washed 1× with 300 mL portions of 2M KOH, 2× with $H_2O$ containing 10% brine to aid phase separation and with brine 2× prior to drying over $Na_2SO_4$. After removal of the volatiles, the residue was recrystallized from absolute EtOH to yield 230 g of 5-bromo-2-chloro-4'-ethoxydiphenylmethane as a white solid.

C.

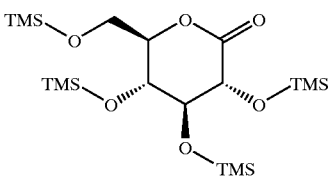

C. 2,3,4,6-tetra-O-Trimethylsilyl-β-D-glucolactone

To a stirred $-5°$ C. solution of gluconolactone (239 g, 1.34 mol and N-methylmorpholine (1180 mL, 10.73 mol) in 2.4 L of THF under Ar was added trimethylsilyl chloride (1022 mL, 8.05 mol) via dropping funnel at a rate such that the temperature did not exceed 5° C. After 1 hr the stirred reaction was heated to 35° C. for 5 hr whereupon it was allowed to cool to 20° C. as the reaction stirred overnight. After dilution with 3.6 L of toluene, the mixture was cooled to 0–5° C. prior to cautiously adding 7 L of $H_2O$ at a rate such that the temperature did not exceed 10° C. Note, a severe exotherm results upon addition of the first portion of $H_2O$. After mixing, the phases were allowed to separate and then split. The organic phase was washed with aq. $NaH_2PO_4$ (2 L), $H_2O$ (1 L), and brine (1 L). The organic layer was then concentrated under vacuum using a rotary evaporator; the resultant light yellow oil was twice taken up 250 mL of toluene and reconcentrated to yield 616 g of title compound.

D.

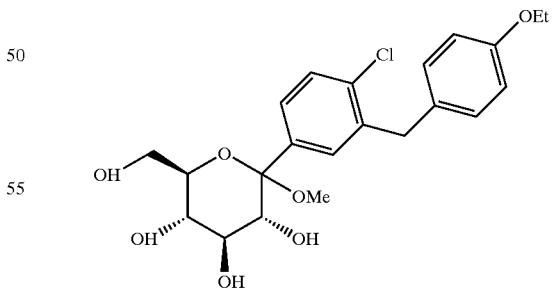

To a stirred $-78°$ solution of Part B 5-bromo-2-chloro-4'-ethoxydiphenylmethane (150 g, 0.46 mol) in 1.15 L of 1:2 dry THF/toluene under Ar was added 184 mL of 2.5 M n-BuLi in hexane dropwise to insure the temperature remained below $-70°$. After stirring for 30 minutes following the addition, this solution was transferred by cannula to a stirred $-78°$ solution of Part C 2,3,4,6-tetra-O- trimethylsilyl-β-D-glucolactone (236 g, 0.51 mol) in 1.1 L of toluene at a rate that maintained the reaction below −70°. The solution was stirred for 30 min at −78° prior to quenching by addition of 1 L of MeOH containing methanesulfonic acid (41.8 mL, 0.64 mol). The reaction stirred overnight as the temperature rose to 20° C. HPLC analysis reveals two new peaks corresponding to the mass of the expected O-methylglucoside; the ratio typically varies from 95:5 to 80:20. The desired product corresponds to the major one with shorter retention time. Note longer reaction times or addition of 50% more methanesulfonic acid will convert all of the isomeric product to the desired O-methylglucoside. The reaction, once complete, was quenched by the addition of $NaHCO_3$ (37 g, 0.37 mol) in 200 mL of $H_2O$. If the pH was not weakly basic, more $NaHCO_3$ was added prior to dilution 2 fold with $H_2O$ and 3 extractions with EtOAc. The combined EtOAc fractions were washed with brine and dried over $Na_2SO_4$. After concentration using a rotary evaporator, the residue was dissolved in hot toluene (150 mL). The resulting solution was poured into a liter of stirred hexane. The precipitate was collected by vacuum filtration; the resulting filter cake was washed 2× with 500 mL of hexane and then air dried to yield 171 g of title compound in the form of a white solid.

E.

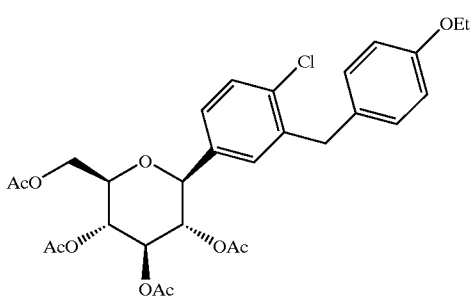

To a stirred −10° solution of Part D O-methylglucoside (123 g, 0.28 mol) in 1.2 L of 1:1 $CH_2Cl_2$/MeCN was added $Et_3SiH$ (65.27 g, 0.56 mol) followed by addition of $BF_3.Et_2O$ (59.75 g, 0.42 mol) at a rate such that the temperature was maintained between −5°—−10°. The stirred solution was allowed to warm to 0° over 5 hr. When HPLC analysis revealed that the reaction was complete, the reaction was quenched by addition of satd. aq $NaHCO_3$ (310 mL). The organic volatiles were removed under vacuum using a rotary evaporator. The residue was partitioned between 2 L each of EtOAc and $H_2O$. After separating phases, the $H_2O$ layer was extracted 2× with 2 L portions of EtOAc. The combined organic phases were washed with $H_2O$ (2 L) and with brine (2 L) prior to drying over $MgSO_4$ and then concentrated using a rotary evaporator to yield 104.6 g of yellow solidified foam. After dissolution of this residue in $CH_2Cl_2$ (750 mL), pyridine (200 g, 2.53 mol) was added followed by $Ac_2O$ (261.1 g, 2.56 mol) in one portion. After the resulting exotherm raising the temperature from 28° to 47° had subsided, DMAP (1.56 g, 13 mmol) was added. The reaction was quenched after 1.5 hr by addition of $H_2O$ (1.8 L) once HPLC analysis indicated the reaction to be complete. The mixture was extracted 2× with $CH_2Cl_2$ (total volume 2.7 L); the combined organic layers were washed 2× with 1N HCL (1.8 L), 2× with brine (1.8 L) prior to drying over $MgSO_4$. The residue, after concentration using a rotary evaporator, was recrystallized from absolute EtOH (750 mL) to yield 89.5 g of the desired tetraacetylated β-C-glucoside as a white solid. The mother liquors contained the corresponding α-C-glucoside as well as a more polar furanose isomer.

F.

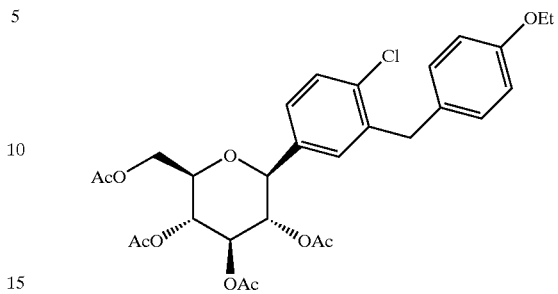

Alternatively the O-methylglucoside of Part D can first be aceylated and then reduced to yield the desired tetraacetylated C-arylglucoside utilizing the following procedure.

A solution of Part D O-methylglucoside (3.0 g, 6.8 mmol) in toluene (45 mL) containing diisopropylethylamine (6.9 mL, 40 mmol) was cooled to 0° prior to addition of acetic anhydride (3.35 mL, 35.5 mmol) and DMAP (84 mg, 0.68 mmol). The solution was allowed to gradually warm to 20°; after six hours, tlc analysis revealed complete conversion to tetraacetate. The reaction was quenched by addition of 50 mL of 20% $H_3PO_4$. After separation of the layers, the aq. phase was extracted 2× with toluene. The combined organic phases were washed 1× with 50 mL of $H_2O$ prior to concentration under vacuum. The resultant oil was dissolved in 20 mL of toluene and reconcentrated to yield a thick oil (4.15 g) that was used without further purification.

A solution of the above crude oil(4.15 g, 6.8 mmol) in MeCN (60 mL) containing one eqivalent of $H_2O$ (123 mg, 6.8 mmol) was cooled to 0° prior to addition of $Et_3SiH$ (3.27 mL, 20.5 mmol) followed by $BF_3.Et_2O$ (1.73 mL, 13.7 mmol). After stirring for 1 hr, the solution was allowed to warm to 20°. After 4 hr, once periodic HPLC analysis revealed that the reaction was no longer progressing beyond 60%, an additional 2 mL of $Et_3SiH$ and 1 mL of $BF_3.Et_2O$ was added. Two hours later, no starting material remained by HPLC analysis. After adding aq $NaHCO_3$ to quench the reaction, the mixture was stirred 30 min prior to being extracted 3× with EtOAc. The combined organic layers were washed 1× with aq $NaHCO_3$ and brine prior to drying over $Na_2SO_4$. The oil obtained after concentration under vacuum was dissolved in 70 mL of hot 25% EtOAc/hexane. Upon cooling, 2.45 g of desired tetraacetylated β-C-arylglucoside crystallized which was subsequently isolated by filtration.

G.

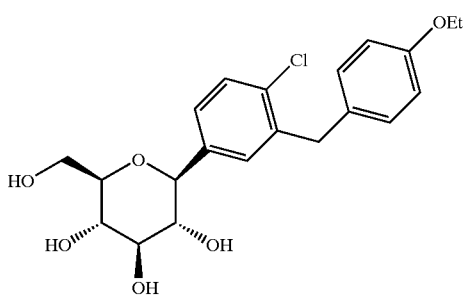

To a stirred 20° solution of tetraacetylated β-C-glucoside (27.2 g, 49 mmol) (prepared as described in Part E), in 480 mL of 2:3:1 THF/MeOH/$H_2O$ was added $LiOH.H_2O$ (2.3 g, 57 mmol). After stirring overnight, the volatiles were removed using a rotary evaporator. The residue, after being dissolved in EtOAc (300 mL), was washed 1× with brine (150 mL), 1× with brine (50 mL) containing 10 mL of 5% aq KHSO4 and finally with brine (50 mL) prior to drying over $Na_2SO_4$. The volatiles were removed using a rotary evaporator and the resultant oil in the minimum amount of $CH_2Cl_2$ foamed under vacuum to yield 20.4 g of desired title C-arylglucoside as a glassy off white solid containing 0.11 mol % of EtOAc.

HPLC retention time: 7.08 min, 94% pure, YMC S5 C-18 4.6×50 mm column, 2.5 mL/min, detection at 220 nM; 8 min gradient 0–100% B hold 5 min at 100% B. Solvent A: 10% $MeOH/H_2O$+0.2% $H_3PO_4$. Solvent B: 90% $MeOH/H_2O$+ 0.2% $H_3PO_4$.

$^1$H NMP (500 MHz, $CD_3OD$) δ7.33 (d, 1H, J=6 Hz), 7.31 (d, 1H, J=2.2 Hz), 7.31 (dd, 1H, J=6 Hz, J=2.2 Hz), 7.07 (d, 2H, J=8.8 Hz), 6.78 (d, 2H, J=8.8 Hz), 4.07–3.90 (m, 7H), 3.85 (d, 1H, J=10.6 Hz), 3.69 (dd, 1H, J=5.3, 10.6 Hz), 3.42–3.25 (m, 4H) Hz), 1.34 (t, 3H, J=7 Hz).

$^{13}$C NMP (125 MHz, $CD_3OD$) δ158.8, 140.0, 139.9, 134.4, 132.9, 131.9, 130.8, 130.1, 128.2, 115.5, 82.9, 82.2, 79.7, 76.4, 71.9, 64.5, 63.1, 39.2, 15.2.

Anal Calcd for $C_{21}H_{25}ClO_6$ LC-MS [M+Na$^+$]431; found 431.

What is claimed:
1. A compound having the structure

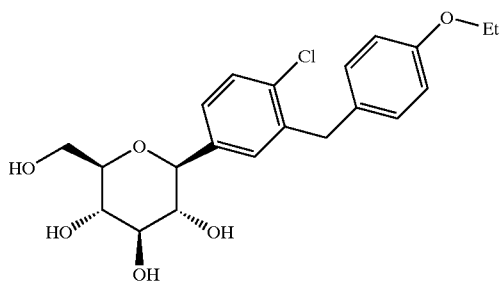

or a pharmaceutically acceptable salt, a stereoisomer thereof, or a prodrug ester thereof.

2. The compound as defined in claim 1 having the structure

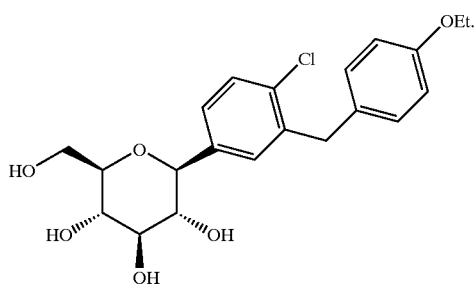

3. A pharmaceutical composition comprising a compound as defined in claim 1 and a pharmaceutically acceptable carrier therefor.

4. A pharmaceutical combination comprising an SGLT2 inhibitor compound as defined in claim 3 and an antidiabetic agent other than an SGLT2 inhibitor, an agent for treating the complications of diabetes, an anti-obesity agent, an antihypertensive agent, an antiplatelet agent, an antiatherosclerotic agent, and/or a lipid-lowering agent.

5. The pharmaceutical combination as defined in claim 4 comprising said SGLT2 inhibitor compound and an antidiabetic agent.

6. The combination as defined in claim 5 wherein the antidiabetic agent is 1, 2, 3 or more of a biguanide, a sulfonyl urea, a glucosidase inhibitor, a PPAR γ agonist, a PPAR α/γ dual agonist, an aP2 inhibitor, a DP4 inhibitor, an insulin sensitizer, a glucagon-like peptide-1 (GLP-1), insulin, a meglitinide, a PTP1B inhibitor, a glycogen phosphorylase inhibitor, and/or a glucos-6-phosphatase inhibitor.

7. The combination as defined in claim 6 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, and/or NVP-DPP-728A.

8. The combination as defined in claim 5 wherein the SGLT2 inhibitor compound is present in a weight ratio to the antidiabetic agent within the range from about 0.01 to about 300:1.

9. The combination as defined in claim 4 wherein the anti-obesity agent is a beta 3 adrenergic agonist, a lipase inhibitor, a serotonin (and dopamine) reuptake inhibitor, a thyroid receptor beta compound, and/or an anorectic agent.

10. The combination as defined in claim 9 wherein the anti-obesity agent is orlistat, ATL-962, AJ9677, L750355, CP331648, sibutramine, topiramate, axokine, dexamphetamine, phentermine, phenylpropanolamine, and/or mazindol.

11. The combination as defined in claim 4 wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor.

12. The combination as defined in claim 11 wherein the lipid lowering agent is pravastatin, lovastatin, simvastatin, atorvastatin, cerivastatin, fluvastatin, nisvastatin, visastatin, atavastatin, rosuvastatin, fenofibrate, gemfibrozil, clofibrate, avasimibe, TS-962, MD-700, and/or LY295427.

13. The combination as defined in claim 11 wherein the SGLT2 inhibitor is present in a weight ratio to the lipid-lowering agent within the range from about 0.01 to about 300:1.

14. A method for treating or delaying the progression or onset of diabetes, diabetic retinopathy, diabetic neuropathy, diabetic nephropathy, delayed wound healing, insulin resistance, hyperglycemia, hyperinsulinemia, elevated blood levels of fatty acids or glycerol, hyperlipidemia, obesity, hypertriglyceridemia, Syndrome X, diabetic complications, atherosclerosis or hypertension, or for increasing high density lipoprotein levels, which comprises administering to a mammalian species in need of treatment a therapeutically effective amount of a compound as defined in claim 1.

15. The method as defined in claim 14 where the SGLT2 inhibitor compound has the structure

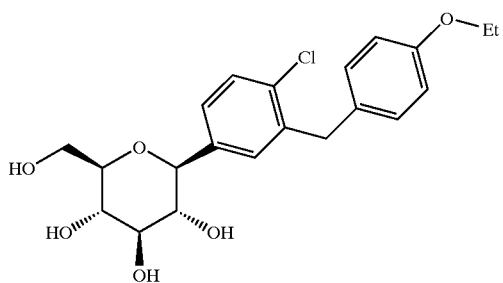

16. A method for treating type II diabetes which comprises administering to a mammalian species in need of treatment a therapeutically effective amount of a compound as defined in claim 1 alone or in combination with another antidiabetic agent, an agent for treating the complications of diabetes, an anti-obesity agent, an antihypertensive agent, an antiplatelet agent, an anti-atherosclerotic agent and/or a hypolipidemic agent.

17. A compound having the structure

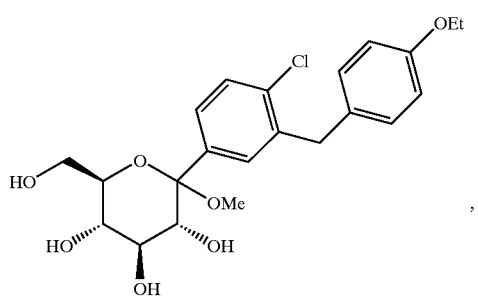

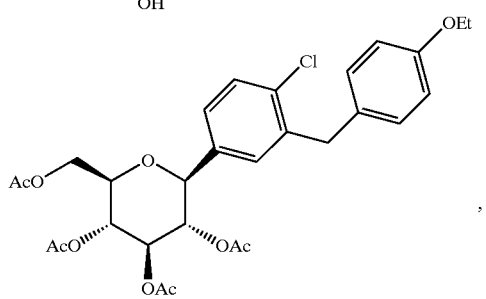

or a pharmaceutically acceptable salt thereof, all stereoisomers thereof, or a prodrug ester thereof.

* * * * *

UNITED STATES PATENT AND TRADEMARK OFFICE
Certificate

Patent No. 6,515,117 B2                                                       Patented: February 4, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bruce Ellsworth, Princeton, NJ (US); Wiliam N. Washburn, Titusville, NJ (US); and Wei Meng, Pennington, NJ (US).

Signed and Sealed this Twenty-fifth Day of November 2008.

<div style="text-align:right">

S. A. JIANG
*Supervisory Patent Examiner*
Art Unit 1623

</div>

UNITED STATES PATENT AND TRADEMARK OFFICE

(12)        CERTIFICATE EXTENDING PATENT TERM
UNDER 35 U.S.C. § 156

| | | | |
|---|---|---|---|
| (68) | PATENT NO. | : | 6,515,117 |
| (45) | ISSUED | : | February 4, 2003 |
| (75) | INVENTOR | : | Ellsworth et al. |
| (73) | PATENT OWNER | : | AstraZeneca AB |
| (95) | PRODUCT | : | FARXIGA® (dapagliflozin) |

This is to certify that an application under 35 U.S.C. § 156 has been filed in the United States Patent and Trademark Office, requesting extension of the term of U.S. Patent No. 6,515,117 based upon the regulatory review of the product FARXIGA® (dapagliflozin) by the Food and Drug Administration. According to United States Patent and Trademark Office records, the original expiration date of the patent as of the date of issuance of this certificate is October 4, 2020. Because it appears that the requirements of the law have been met, this certificate extends the term of the patent for the period of

(94)                                5 years subject to the payment of maintenance fees as provided by law, with all rights pertaining thereto as provided by 35 U.S.C. § 156.

I have caused the seal of the United States Patent and Trademark Office to be affixed this 29th day of July 2020.

Andrei Iancu
Under Secretary of Commerce for Intellectual Property and
   Director of the United States Patent and Trademark Office